(12) United States Patent
Urbahns et al.

(10) Patent No.: US 6,264,657 B1
(45) Date of Patent: Jul. 24, 2001

(54) METHOD FOR REMOVING DEVICES FROM BONE

(75) Inventors: David J. Urbahns, Beachwood, OH (US); Thomas S. Camino, Warsaw, IN (US)

(73) Assignee: Depuy Acromed, Inc., Cleveland, OH (US)

( * ) Notice: Subject to any disclaimer, the term of this patent is extended or adjusted under 35 U.S.C. 154(b) by 0 days.

(21) Appl. No.: 09/293,115

(22) Filed: Apr. 16, 1999

Related U.S. Application Data

(60) Provisional application No. 60/082,483, filed on Apr. 21, 1998.

(51) Int. Cl.[7] ..................................................... A61B 17/56
(52) U.S. Cl. ................................................................ 606/61
(58) Field of Search ................................. 606/96, 61, 90, 606/87; 623/17

(56) References Cited

U.S. PATENT DOCUMENTS

| | | | |
|---|---|---|---|
| 4,059,115 | 11/1977 | Jumashev et al. . | |
| 4,069,824 | 1/1978 | Weinstock . | |
| 4,150,675 | 4/1979 | Comparetto . | |
| 4,696,308 | 9/1987 | Meller et al. . | |
| 5,015,247 | * 5/1991 | Michelson ............................ | 606/61 |
| 5,197,967 | 3/1993 | Wilson . | |
| 5,484,437 | * 1/1996 | Michelson ............................ | 606/61 |
| 5,489,307 | * 2/1996 | Kuslich et al. ...................... | 606/96 |
| 5,653,762 | * 8/1997 | Pisharodi ............................. | 606/61 |
| 5,683,391 | * 11/1997 | Boyd ................................... | 606/61 |
| 5,797,917 | 8/1998 | Boyd et al. . | |
| 5,961,522 | * 10/1999 | Mehdizadeh ........................ | 606/79 |

FOREIGN PATENT DOCUMENTS

| | | |
|---|---|---|
| 0 307 241 | 3/1989 | (EP) . |
| WO 95/25487 | 9/1995 | (WO) . |
| WO 96/27345 | 9/1996 | (WO) . |

OTHER PUBLICATIONS

"Putting You In Charge. Restore™ ACL Reconstructive Guide System", ©1995 DePuy Inc., brochure #20M0295, 6 pages.

\* cited by examiner

*Primary Examiner*—Henry J. Recla
*Assistant Examiner*—Tan-Uyen T. Ho

(57) ABSTRACT

A kit is for removing a spacer having a surface and ends from a spine. The kit includes an osteotome, a threaded extractor, and a trephine, each for releasing spacer from spine. Osteotome includes a cutting portion having a surface formed to engage surface of spacer and a tip formed to cut bone surrounding surface of spacer. Extractor includes a side wall having threads formed to cut one of the ends of spacer and pull spacer away from spine when side wall rotates relative to spacer. Trephine includes a blade having a sleeve defining a passageway and including an edge formed to cut material surrounding surface of spacer.

14 Claims, 2 Drawing Sheets

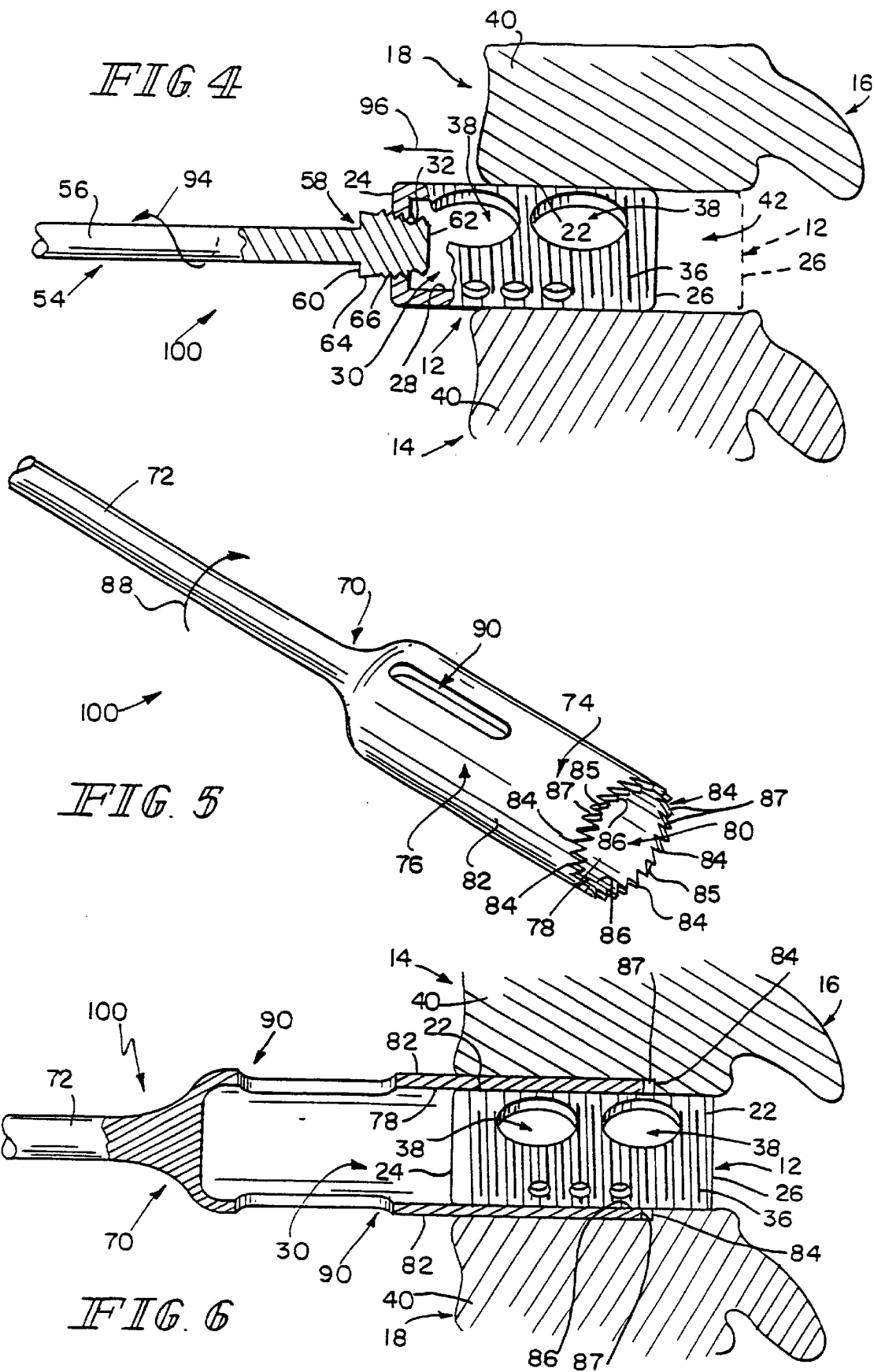

METHOD FOR REMOVING DEVICES FROM BONE

This application claims priority under 35 U.S.C. § 119(e) of Ser. No. 60/082,483 filed Apr. 21, 1998 in the United States Patent and Trademark Office.

BACKGROUND AND SUMMARY OF THE INVENTION

This invention relates to the removal of devices from bone, more particularly, to the removal of implanted devices from a spine. Most particularly, the present invention relates to a kit for use in removing implanted devices from a spine.

According to the present invention, a kit and method are provided for removing a spacer having an outer surface and opposite ends from a spine. The kit includes an osteotome, a threaded extractor, and a trephine. The osteotome includes a handle portion and a cutting portion that extends from the handle portion and has a surface formed to engage the outer surface of the spacer and a tip spaced-apart from the handle portion. The tip is formed to cut material surrounding the outer surface of the spacer to release the spacer from the spine. The threaded extractor includes a handle and an end portion coupled to the handle. The end portion includes a side wall with threads formed to cut into one of the ends of the spacer and pull the spacer toward the handle upon rotation of the side wall relative to the spacer releasing the spacer from the spine. Further, the trephine includes a blade that has a sleeve with an inner surface that defines a passageway sized for reception of the spacer therein, an outer surface, and an edge positioned at the periphery of an opening into the passageway. The edge is formed to cut material surrounding the outer surface of the spacer.

The method of the present invention involves the use of the kit and components thereof to remove such a spacer from the spine by cuting the bone about the outer surface of the spacer.

Additional features of the present invention will become apparent to those skilled in the art upon consideration of the following detailed description of preferred embodiments exemplifying the best mode of carrying out the invention as presently perceived.

BRIEF DESCRIPTION OF THE DRAWINGS

FIG. 4 is a view similar to FIG. 3 showing the threads of the reverse-thread extractor cutting into the lip of the spacer and counter-clockwise rotation of the handle causing movement of the spacer out from the cavity;

FIG. 5 is a perspective view of a trephine including a handle and a cutting end having a sleeve defining a passageway sized for reception of the fusion cage therein and showing the cutting teeth extending about the periphery of an opening into the passageway; and FIG. 6 is a view similar to FIG. 2 showing the fusion cage extending into the passageway of the trephine and the teeth machining around the outer side of the fusion cage to disconnect the fusion cage from the bone.

DETAILED DESCRIPTION OF THE INVENTION

Figure 1:
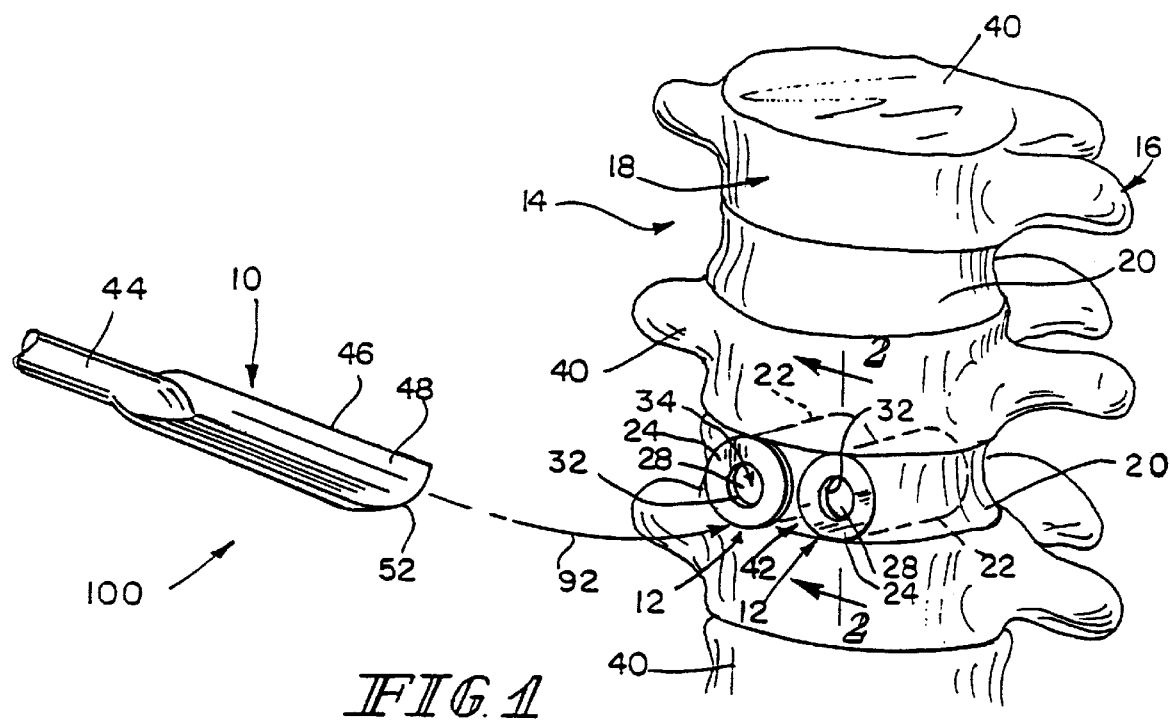
FIG. 1 is a prospective view of an anterior portion of a spine with a portion of one disc removed to form a cavity, spacers positioned to lie within the cavity between the vertebral bodies, and an osteotome including a cutting tip formed to cut around the spacer.
Figure 3:
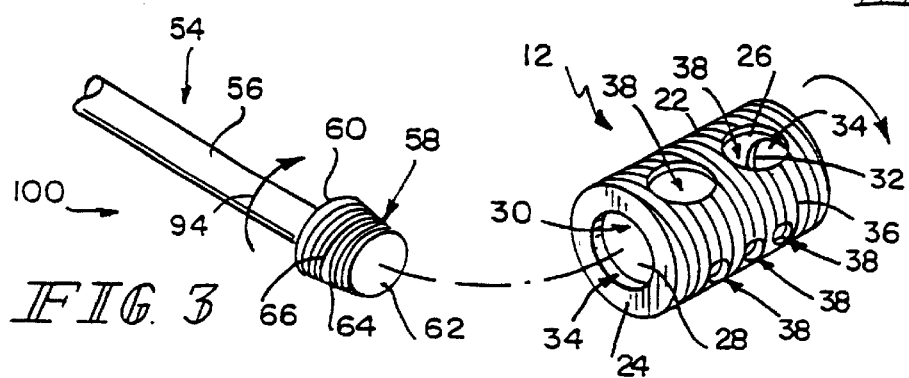
FIG. 3 is a perspective view of a reverse-thread extractor and the fusion cage and showing the fusion cage including an inner surface defining a passageway and the reverse-thread extractor including a handle and a tapered end portion having counter-clockwise threads.

A revision instrument kit 100 and method are provided in accordance with the present invention for removing devices such as vertebral body spacers 12 from a spine 14 during disc-replacement surgery. As shown in FIGS. 1, 3, and 5, instrument kit 100 permits a surgeon to remove spacers 12 from an anterior portion 18 of spine 14 while cutting only a limited amount of bone surrounding spacer 12. This removal may be done to replace an inter-vertebral discs 20. Revision instrument kit 100 includes an osteotome 10, an easy-out or reverse-thread extractor 50, and a trephine 110.

Spacers 12 include threaded fusion cages that are constructed of metal and implanted generally horizontally into the spine 14. See FIGS. 1–2. Each spacer 12 houses packed bone or other desired materials (not shown) therein so that spacer 12 fuses to spine 14 and generally prevents movement between the two vertebrae 40 to reduce a patient's pain. It is appreciated that revision instrument kit 100 may be used with variety of spacers constructed in a variety of sizes and from a variety of materials such as tissue, bone, composites, or the like designed to be placed into spine 14 as a spinal spacer.

Figure 2:
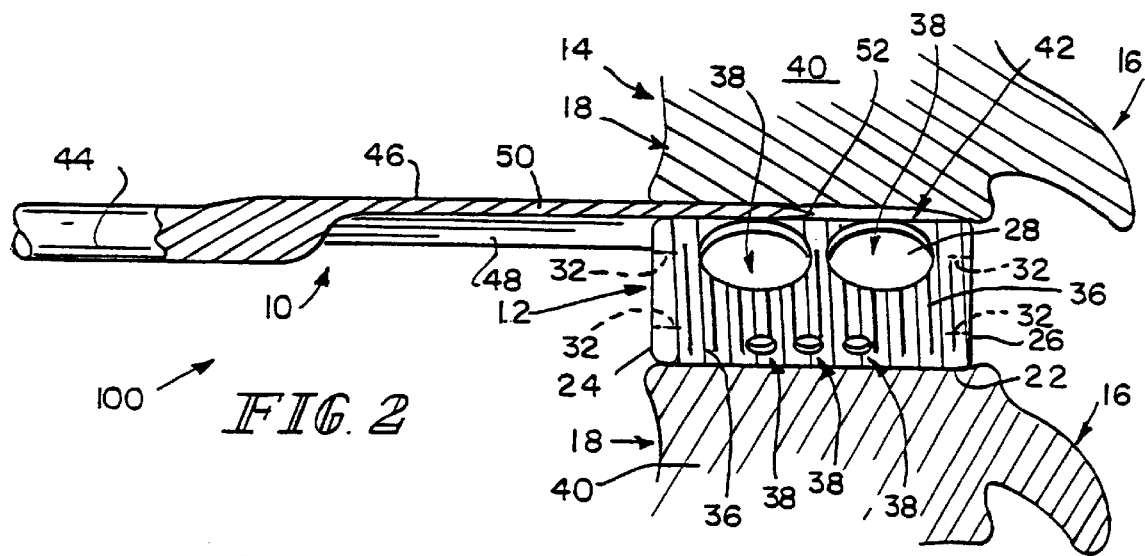
FIG. 2 is a view taken along lines 2—2 of FIG. 1 showing the fusion cage including an outer surface having clockwise threads thereon and apertures formed through the outer surface and the cutting tip of the osteotome extending into the cavity between one vertebral body and the fusion cage to release the fusion cage from the bone.

Referring now to FIGS. 1, 2 and 3, illustrative spacer 12 includes a generally cylindrical outer surface 22, opposite ends 24, 26, and an inner surface 28 defining a passageway 30 extending between the opposite ends 24, 26 and sized to receive the packed bone. Each end 24, 26 is formed to include a lip 32 defining an aperture 34 having a diameter less than the diameter of passageway 30. In addition, spacer 12 includes threads 36 formed on outer surface 22 as well as holes 38 of various size extending between outer and inner surfaces 22, 28. It is appreciated that spacer 12 may include threads that extend in a clock-wise or counter-clockwise direction and may be formed without holes 38.

Spine 14 includes anterior portion 18 and a posterior portion 16. See FIGS. 1 and 2. In addition, spine 14 includes cervical, thoracic, and lumbar vertebral bodies 40. Instruments 10, 54, 70 of revision instrument kit 100 are configured to remove illustrative spacers 12 from discs 20 of the anterior and poster portions 18, 16 of spine 14 whether it is cervical, thoracic or lumbar. After removing spacer 12, the surgeon removes all of the damaged disc or a portion thereof and reams away bone on either side of disc 20. New spacer 12 is then delivered into a resulting cavity 42 to replace disc 20 and dig into adjacent vertebral bodies 40. Spacers 12 are positioned to lie in a side-by-side relation within cavity 42. See FIG. 1.

Osteotome 10 of revision instrument kit 100 is provided for removing spacer 12 from spine 14 with minimal invasiveness. As shown in FIGS. 1–2, osteotome 10 includes a handle portion 44 and a cutting portion 46. Cutting portion 46 includes a generally concave inner surface 48 and an outer surface 50. Cutting portion 46 also includes a tip 52. Tip 52 is formed to chisel around outer surface 22 of spacer 12 to release spacer 12 from vertebral bodies 30 for whatever reason spacer 12 is being removed from spine 14. While osteotome 10 is illustrated and described, it is appreciated that a variety of commercially available osteotomes, including osteotomes having an inner surface formed such that it corresponds with various shaped spacers, tips that vary in size and shape, and handles with pre-set angles or handles that are configured to move to various angles are contemplated in the present disclosure.

Reverse threaded extractor 54 of revision instrument kit 100 is provided for use when greater invasiveness than that provided by osteotome 10 is necessary to remove spacer 12 from spine 14. While the extent of invasiveness is increased by the use of extractor 54 over osteotome 10, the invasiveness of the removal of spacer 12 with extractor 54 is still limited. Extractor 54 is configured to pull spacer 12 out from either anterior or posterior portions 18, 16 of spine 14. Extractor 54 includes a handle 56 and an end portion 58. End portion 58 includes a base 60, a tip 62, and a side wall 64 converging from base 60 toward tip 62. Side wall 64 includes threads 66 formed thereon. Extractor 54 is constructed of a high grade stainless steel. It is appreciated, however, that extractor 54 may be constructed of a variety of medical-grade materials so long as threads 66 are relatively harder than the material of which spacer 12 is constructed and extend in the opposite direction of threads 36 formed on outer surface 22 of spacer 12. Threads may extend about side wall 64 in a clock-wise or counter clockwise manner in accordance with the present disclosure.

Trephine 70 of revision instrument kit 100 is provided for use when spacer 12 is fused to spine 14 such that greater invasiveness than that provided by extractor 54 is necessary to remove spacer 12 from spine 14. Trephine 70 is shown in FIGS. 5–6. Trephine 70 is formed to cut around spacer 12 to disconnect from spine 14 so that spacer 12 can be easily removed in accordance with the method of the present invention. Trephine 70 is constructed of stainless steel, although other materials can be used in accordance with the present disclosure.

Trephine 70 includes a handle 72 and a blade 74. As best shown in FIG. 5, blade 74 includes a sleeve 76 that has an inner surface 78 that defines a passageway 80 sized for reception of spacer 12 therein, an opposite outer surface 82, and an edge 68 extending about the periphery of an opening 86 into passageway 80. Edge 68 is preferably defined by spaced-apart teeth 84. Each tooth 84 includes a first side 85 positioned to extend in general alignment with outer surface 82 of blade 80 and a second side 87 positioned to lie at an angle off-set from first side 85 such that second side 87 intersects first side 85 at peak 89. First and second sides 85, 87 of teeth 84 are positioned to lie in a counter-clockwise manner so that bone surrounding spacer 12 is cut upon rotation of handle 72, as shown by arrow 88, in a clock-wise direction to cut bone. It is appreciated that the configuration of first and second sides 85, 87 of teeth may vary depending upon the desired direction of rotation of handle 72.

In addition, inner surface 78 of trephine 70 is sized so as to engage threads 36 on outer surface 22 of spacer 12. See FIG. 6. The engagement between trephine 70 and spacer 12 minimizes the amount of distributed bone surrounding spacer 12. Slots 90 are also formed in blade 74 between inner and outer surfaces 78, 82. It is appreciated that a variety of trephines having handles of various lengths, blades of various lengths and diameters, and blades with a pointed tip rather than spaced-apart teeth may be used in accordance with this disclosure.

Therefore, revision instrument kit 100 is provided in accordance with the present invention for removing implanted spacers 12 from spine 14. The user will receive kit 100 that includes osteotome 10, extractor 54, and trephine 70. Once the user has determined the relative dimensions of the spacer 12 to be removed, the appropriate kit 100 for use with the environment may be selected. It is contemplated that osteotome 10, extractor 54, and trephine 70 that make up kit 100 will have similar dimensions that correspond to the dimensions of known spacers 12.

In use, the user will select kit 100 whose components correspond in shape and size to the implanted spacer 12. Based upon the amount of fusion between spacer 12 and vertebrae 40, the user may select to use one or more of osteotome 10, extractor 54, or trephine 70 to remove spacer 12 from spine 14. Moreover, it is appreciated that the user may began removal of spacer from spine 14 with one of the osteotome 10, extractor 54, or trephine 70 and complete the removal with one or more of the osteotome 10, extractor 54, or trephine 70.

Referring now to FIG. 1, tip 52 of osteotome 10 is first positioned as shown by arrow 92 along outer surface 22 of spacer 12 between vertebral body 40 and spacer 12. At this time, inner surface 48 of cutting portion 46 faces spacer 12 and outer surface 50 of cutting portion 46 faces adjacent vertebral body 40. See FIG. 2. Cutting portion 46 of osteotome 10 is maneuvered about outer surface 22 of spacer 12 to chisel the surrounding soft and hard bone or other fibrous tissue. Once cutting portion 46 has chiseled away the bone fused to spacer 12, spacer may be pulled from cavity 42 away from spine 14. It is appreciated that by chiseling only bone immediately surrounding spacer 12 provides a relatively limited invasive method for removing spacer 12 from spine 14.

If greater invasiveness than that provided by osteotome 10 is necessary to remove spacer 12 from spine 14, the user may select extractor 54 from kit 100. To remove spacer 12 from spine 14 using extractor 54, tip 62 is inserted into aperture 34. Handle 56 is then turned as shown by arrow 94 so that threads 66 engage lip 32 of spacer 12. As handle 56 is turned, threads 66 dig into lip 32 of spacer 12 and couple extractor 54 and spacer 12 together. Threads 66 dig into lip 32 because threads 66 are constructed of material that is harder than the material of which spacer 12 is constructed. As the user continues turning handle 56 in the direction of arrow 94, spacer 12 begins to move as shown by arrow 96 generally horizontally from between vertebral bodies 40 and away from spine 14.

If still greater invasiveness than that provided by extractor 54 is necessary to remove spacer 12 from spine 14, the user may select trephine 70 from kit 100. To remove spacer 12 from spine 14 using trephine 70 in accordance with the present invention, blade 74 is first positioned to lie adjacent spacer 12. See FIGS. 5 and 6. The user then rotates handle 72 as shown by arrow 88. As handle 72 is turned in the direction of arrow 88, edge 68 digs into the bone 40 and disconnects spacer 12 from spine 14 to allow for removal of spacer 12. As best shown in FIG. 6, as handle is turned, spacer 12 extends into passageway 89 of trephine 70 and teeth 84 cut around outer surface 22 to disconnect spacer 12 from between vertebral bodies 40. At this point, spacer 12 may be pulled away from spine 14 with trephine 70 or spacer 12 may be pulled away from spine 14 on its own.

Although the invention has been described in detail with reference to a preferred embodiment, variations and modifications exist within the scope and spirit of the invention as described and defined in the following claims.

What is claimed is:

1. A kit for removing a vertebral body spacer having a predetermined length and having an outer surface and opposite ends from a spine, the kit comprising an osteotome including a handle portion and a cutting portion extending from the handle portion and having a surface formed to engage the outer surface of the vertebral body spacer and a tip spaced-apart from the handle portion of sufficient length to cut material surrounding substantially the entire length of the outer surface of the vertebral body spacer to release the spacer from the spine, a threaded extractor including a handle and an end portion coupled to the handle, the end portion including a side wall having threads formed to cut into one of the ends of the vertebral body spacer and pull the vertebral body spacer toward the handle upon rotation of the side wall relative to the vertebral body spacer releasing the vertebral body spacer from the spine, and a trephine including a blade having a sleeve with an inner surface defining a passageway sized for reception of the vertebral body spacer therein, an outer surface, and an edge positioned at the periphery of an opening into the passageway, and the edge is formed to cut material surrounding the outer surface of the vertebral body spacer.

2. The kit of claim 1, wherein the edge of the trephine includes teeth.

3. The kit of claim 1, wherein the trephine includes a handle coupled to the blade.

4. The kit of claim 1, wherein the end portion of the extractor includes a base, a tip, and the side wall extends between the base and the tip.

5. The kit of claim 4, wherein the side wall converges from the base toward the tip.

6. A method for removing from a spine a vertebral body spacer which has become fused to the spine comprising the steps of:

providing an osteotome including a cutting portion having an inner surface formed to engage the outer surface of the vertebral body spacer and a tip adjacent to the inner surface, inserting the tip into the spine adjacent to the vertebral body spacer, positioning the inner surface adjacent to the outer surface of the the vertebral body spacer, and moving the tip about the outer surface of the vertebral body spacer to cut the surrounding bone after the vertebral body spacer has become fused to the spine so as to release the vertebral body spacer from the spine.

7. A method of removing from a spine a vertebral body spacer that includes an outer surface and opposite ends, each end being formed to include a lip defining an aperture, the method comprising the steps of:

providing a threaded extractor having a side wall with threads formed thereon;

inserting the side wall into the aperture of the vertebral body spacer; and rotating the side wall in the aperture after the vertebral body spacer has become fused to the spine so that the threads dig into the lip and pull the vertebral body spacer away from the spine.

8. A method for removing a vertebral body spacer from a spine, comprising the steps of:

maneuvering an osteotome about an outer surface of the vertebral body spacer so as cut bone of the spine after the vertebral body spacer has become fused to the spine; and pulling the vertebral body spacer away from the spine after the maneuvering step.

9. The method of claim 8, wherein:

the osteotome includes a cutting portion which possesses an inner surface formed to correspond to an outer surface of the verterbral body spacer, and the maneuvering step includes the step of engaging the outer surface of the verterbral body spacer with the inner surface of the osteotome.

10. The method of claim 8, wherein the vertebral body spacer includes a fusion cage which was implanted into the spine prior to the maneuvering step by an amount of time sufficient to effect fusion between the fusion cage to the spine.

11. The method of claim 8, wherein:

the vertebral body spacer includes a fusion cage which was implanted into the spine, and the fusion cage is configured to house packed bone therein during implantation of the fusion cage into the spine.

12. A method for removing a vertebral body spacer from a spine, with the vertebral body spacer having a passageway defined therein which is adapted to receive packed bone therein, and further with the vertebral body spacer having a circumferential lip, comprising the steps of:

inserting an externally threaded portion of an extractor into the passageway of the vertebral body spacer; and rotating the externally threaded portion after the inserting step so that the externally threaded portion cuts into the circumferential lip of the vertebral body spacer, wherein the rotating step causes the vertebral body spacer to be pulled away from the spine.

13. The method of claim 12, wherein the vertebral body spacer includes a fusion cage which was implanted into the spine prior to the rotating step by an amount of time sufficient to effect fusion between the fusion cage to the spine.

14. The method of claim 12, wherein:

the vertebral body spacer includes a fusion cage which was implanted into the spine, and the fusion cage is configured to the house packed bone therein during implantation of the fusion cage into the spine.

* * * * *